United States Patent [19]

Riemersma et al.

[11] 4,272,473
[45] Jun. 9, 1981

[54] METHOD FOR EMBOSSING AND PERFORATING A RUNNING RIBBON OF THERMOPLASTIC FILM ON A METALLIC PATTERN ROLL

[75] Inventors: Coenraad E. Riemersma; Theodore P. Merz, both of Cincinnati, Ohio

[73] Assignee: The Procter & Gamble Company, Cincinnati, Ohio

[21] Appl. No.: 967,194

[22] Filed: Dec. 7, 1978

[51] Int. Cl.³ .......................................... B29C 17/14
[52] U.S. Cl. .................... 264/154; 264/145; 264/163; 264/284; 264/293; 425/304
[58] Field of Search .............. 264/145, 154, 284, 139, 264/163, 293; 425/290, 304

[56] References Cited

U.S. PATENT DOCUMENTS

| | | |
|---|---|---|
| 2,689,378 | 9/1954 | Muth, Sr. et al. ............... 264/284 |
| 3,214,502 | 10/1965 | Schaar ............................ 264/154 |
| 3,243,488 | 3/1966 | Hannauer, Jr. et al. .......... 264/284 |
| 3,323,983 | 6/1967 | Palmer et al. ................... 264/280 |
| 3,560,601 | 2/1971 | Johnson et al. .................. 264/154 |
| 3,566,726 | 3/1971 | Politis ............................. 264/280 |
| 3,584,572 | 6/1971 | Apicella .......................... 264/163 |
| 3,718,725 | 2/1973 | Hamano .......................... 264/163 |
| 3,753,352 | 8/1973 | McNally .......................... 264/154 |
| 3,917,785 | 11/1975 | Kalwaites ........................ 264/284 |
| 4,151,240 | 4/1979 | Lucas et al. ..................... 264/154 |

FOREIGN PATENT DOCUMENTS 597115   3/1934   Fed. Rep. of Germany ........... 425/363

Primary Examiner—James B. Lowe
Attorney, Agent, or Firm—Fredrick H. Braun; Richard C. Witte; Thomas H. O'Flaherty

[57] ABSTRACT

The invention disclosed is an apparatus and method to make a thermoplastic film embossed with tapered bosses having perforations in the tips of each boss through use of a metallic pattern roll and a heated perforating roll. The apparatus and method allow a film having tapered bosses with decreased cross-sectional areas leading to a perforation to be formed without use of expensive vacuum forming methods.

The invention discloses a film 10 being heated by a heating means 14 to a deformable state and being embossed on an embossing surface 16 of embossing roll 13 under pressure from the silicone rubber surface 33 of first pressure roll 15. The film on the apex of the cone 26 on embossing surface 16 is removed to perforate the cone by perforating roll 17, which is a resilient hollow metal tube heated from a radiant heater mounted on the inside of the hollow metal tube. The perforated film is then embossed a second time by the action of a second embossing roll 18 and then rewound onto a rewind roll.

16 Claims, 7 Drawing Figures

METHOD FOR EMBOSSING AND PERFORATING A RUNNING RIBBON OF THERMOPLASTIC FILM ON A METALLIC PATTERN ROLL

DESCRIPTION

Technical Field

The apparatus and method of this invention relates to embossing thermoplastic film with cone-shaped bosses and perforating the apex of each cone. The embossed and perforated thermoplastic film can be used as a barrier layer which allows liquid to pass through in one direction and prevents its passage back in the other direction, but allows vapor to pass in either direction.

In making the embossed and perforated film, it is essential that the perforations occur at the apex of each cone and that the embossed cone shape be maintained in the film. It is the tapered shape of each cone that imparts the preferential capillary action which allows liquid to pass through the perforated apex of the cone in one direction but prevents liquid from passing through the perforated cone in the other direction. The shape has a decreasing cross section from the base of the boss towards the apex having the perforation.

BACKGROUND OF THE INVENTION

The background art teaches several apparatus and methods for perforating or embossing a thermoplastic sheet. For example, U.S. Pat. No. 3,214,795 issued to Hannauer on Nov. 2, 1965 and U.S. Pat. No. 3,243,488 issued to Hannauer on Mar. 29, 1966 teach an apparatus and method to perforate a thermoplastic sheet by passing it between a pattern roll and a heated roll. Hannauer discloses an apparatus wherein the embossing roll and the pressure roll are heated. Complete contact is maintained between the nip of the pressure roll and the embossing roll through use of a rigid pressure roll mounted on a pivot and a piston device which varies pressure applied to the embossing roll by the pressure roll.

U.S. Pat. No. 3,560,601 issued to Johnson on Feb. 2, 1971 teaches a method to emboss and perforate a fabric backed thermoplastic film. Johnson teaches a two step method wherein the material is first embossed by passing between the nip of a studded embossing roll and a pressure roll which embosses but does not perforate the material. In the second step, the material is perforated by blowing hot gases through the weakened film sections created by embossing to create a perforated material.

U.S. Pat. No. 3,707,102 issued to Huppenthal on Dec. 26, 1972 teaches a film perforating apparatus wherein the film is passed over the perforating roll having a series of hot pins which perforate the film. The perforating roll has a generally cool external surface having apertures which contain heated pins. The contact with the heated pins creates the perforations in the film.

U.S. Pat. No. 3,950,480 issued to Adams on Apr. 13, 1976 teaches a method to emboss a plastic film where a sheet of thermoplastic material is indirectly heated as it is passed between two heaters and is subsequently passed between the nip of an embossing roll and a pressure roll. As the heated film is passed between the nip of the embossing roll and pressure roll, it is embossed.

Canadian Pat. No. 664,640 issued to Wangner on June 11, 1963 teaches a method to emboss a vinyl film on a fabric back wherein the vinyl layer of the film is impressed into a heated moving wire belt.

Defensive Publication No. 544,271 published by Zeisberg on Dec. 24, 1968 teaches a method to create an apertured nonwoven structure from a film fibril sheet. Zeisberg teaches the method of passing a film fibril sheet through a nip between an embossing surface having male bosses and a resilient moving surface, at least one of which is heated. The male bosses on the embossing surface are elongated metal wires. Contact of the thermoplastic film with the male bosses in a heated environment causes the thermoplastic fibers to melt and be extruded away from the male bosses to create a film having elongated perforations with grommet-like structures around each perforation. The film material is then stretched thereby causing the elongated slits to become circular.

None of the above disclosed patents teach a method to create an embossed and perforated thermoplastic sheet having embossed cones wherein the perforations are critically located in the apex of each cone of each boss. Furthermore, these references do not teach a method to perforate and emboss a film using a metallic pattern roll rolling against a resilient flexible heating roll.

DISCLOSURE OF THE INVENTION

The method and apparatus disclosed herein teach a method to make a thermoplastic film having raised bosses with perforated tips. The resulting product can be used in conjunction with an absorbent means to create an absorbent device having the embossed and perforated thermoplastic film placed adjacent and next to the absorbent device with the embossed tapered cones facing into the absorbent material. The perforated film will present to the liquid to be absorbed capillaries having decreasing cross-section which will, through capillary action, draw liquid into the absorbent material.

The method and apparatus disclosed herein teach a new method of perforating and embossing thermoplastic film without the use of a vacuum mechanism. Avoidance of use of a vacuum saves considerable amounts of energy.

The object of the invention is to provide a method and apparatus to manufacture thermoplastic films having a plurality of tapered, cone-shaped bosses having perforated apexes wherein the tapered boss would easily pass liquid in one direction, but not pass liquid in the other direction.

It is a further object of the invention to disclose a method and apparatus to manufacture thermoplastic sheets having a plurality of tapered bosses with perforated apexes which will exhibit capillary action encouraging the flow of liquid in one direction through the thermoplastic film and discouraging the liquid flow through the thermoplastic film in the other direction and yet allow vapor to pass through the bosses.

It is a further object of the invention to teach a method to produce an embossed thermoplastic film having perforated cone tips having the steps of supplying a heated, deformable plastic film to a male patterned embossing surface having a multiplicity of raised knobs having apices which define a raised surface and conforming the thermoplastic film in intimate contact with the raised knobs to produce an embossed film having a multiplicity of raised bosses. The bosses are then perforated by pressing the tips of the raised bosses between the apices of the knobs of the embossing roll and a heated perforating roll while maintaining the film in contact with the embossing surface. The film is then cooled to a less deformable state while still in registration and contact with the raised knobs. The embossed film is then removed from the male patterned embossing surface.

The method disclosed herein also teaches the step of conforming the perforated film to male knobs on the embossing surface a first time before perforation and a second time after the tips of the bosses in the film have been perforated. The method of the current invention teaches that the thermoplastic film will be conformed to the male embossing roll by passing it between the nip of the embossing roll and a first pressure roll prior to perforation. After perforation, while still in intimate contact with the embossing roll, the film passes through the nip between the second pressure roll and the embossing roll to be embossed the second time.

The method of the current invention teaches perforating the bosses in the film by contact with a heated perforating surface of a resilient hollow metal roll wherein the hollow roll is heated by a radiant heater placed within the resilient metal roll.

The apparatus of the instant invention that produces an embossed thermoplastic film and perforates the tips of the bosses has means to supply a continuous thermoplastic film and a means to heat the thermoplastic film to a deformable state. A male patterned embossing roll having a multiplicity of raised knobs defining a cylindrical peripheral surface and a means to conform the thermoplastic film to the raised knobs on the embossing roll produce an embossed film having a multiplicity of raised bosses. A relatively resilient, heated perforating roll held captive against the male patterned embossing roll forms a nip with the cylindrical peripheral surface of the embossing roll to perforate the tips of the bosses. Subsequently, there is a means to cool the embossed film to a less deformable state.

The apparatus of the present invention includes a first and second means to conform the perforated thermoplastic film to the raised bosses of the male patterned embossing roll before the bosses in the film have been perforated and after perforation to retain the embossing.

In the apparatus of the current invention, the first and second means to conform the film to the surface of the embossing roll are a first and second pressure roll.

In the apparatus of the current invention, the heated perforating surface comprises a resilient, hollow perforating roll forming a nip with the embossing roll wherein a thermoplastic film is passed therebetween. The hollow roll is forced against the embossing roll so as to maintain contact with the film across the width of the embossing roll to perforate the tips of the bosses.

DESCRIPTION OF THE DRAWINGS

A preferred embodiment of the disclosed invention can be seen in the following drawing.

While the following disclosure of the preferred embodiments of the current invention illustrates the best mode presently known to the inventor of the method and apparatus of his invention, the inventor does not limit the scope of his invention to the embodiment expressly disclosed, but defines the scope of his invention according to the claims following this specification.

DETAILED DESCRIPTION OF THE INVENTION

Figure 1:
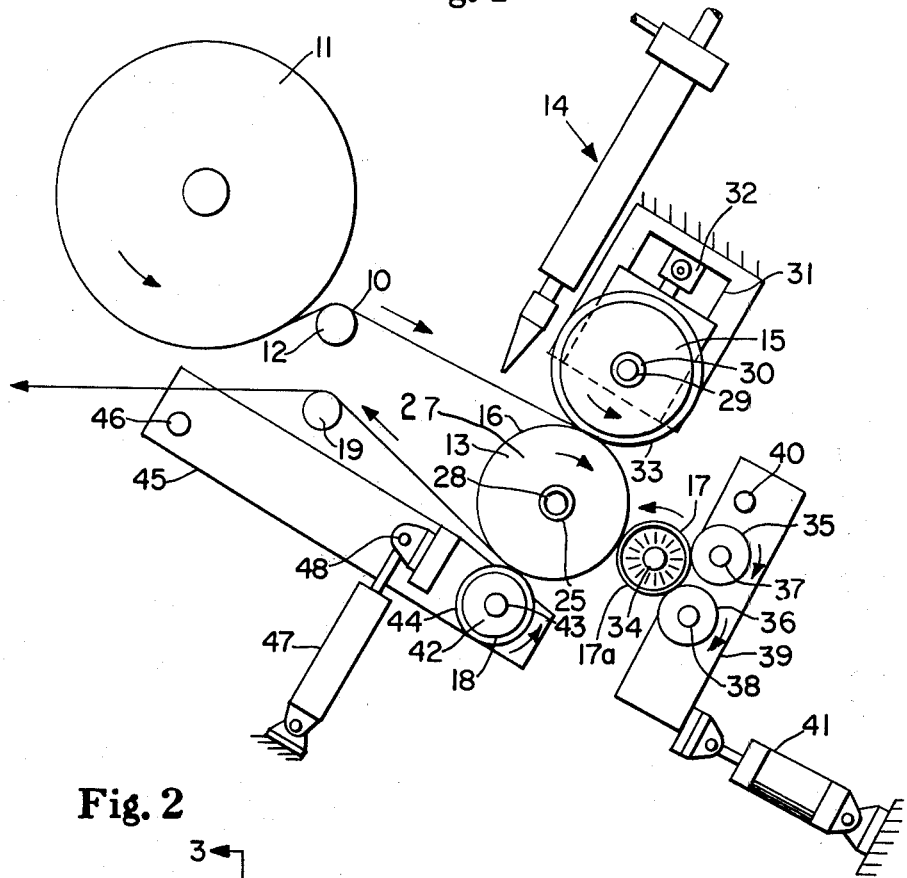
FIG. 1 shows a side elevational view of the preferred embodiment of the apparatus of the invention.

An example of apparatus to make the embossed and perforated film of this invention can be seen in FIG. 1. All elements of the apparatus are attached to a main frame of conventional design which is omitted from the drawings to more clearly show the invention. As seen, a film 10 is taken from a storage means 11, here an unwind roll, and unwound over idler roll 12 onto an embossing roll 13. The film 10 is heated by a heating means 14 prior to contact with embossing roll 13 and is subsequently placed in intimate contact with rotating embossing roll 13. A first pressure roll 15 adjacent embossing roll 13 is in contact with film 10 and applies pressure to film 10 to put film 10 in intimate contact with the embossing surface 16 of embossing roll 13 and to conform to the raised knobs on the male patterned embossing surface 16 of embossing roll 13. The film 10 is pulled forward by the rotation of embossing roll 13 while in intimate contact with embossing surface 16. While the film is still in contacting relation with the embossing surface 16, a perforating roll 17 contacts the film on the raised portions formed in the film conforming to the outer surface 16 of the embossing roll 13 to perforate the apices of the bosses in the film. The film 10 remains in contacting relation with the embossing surface 16 as it rotates with the embossing roll and a second pressure roll 18 contacts the film 10 adjacent embossing roll 13 and causes the perforated film to conform to the surface of the raised knobs of the male patterned embossing surface 16 of embossing roll 13. The film 10 is taken off from embossing roll 13 over idler roll 19 and goes into storage.

The film made by the method and apparatus of the present invention is made from polyethylene film manufactured by VisQueen Division, Ethyl Corporation, Baton Rouge, Louisiana. In the apparatus shown in FIG. 1, the film has a thickness of 0.001 inches (0.025 mm) and has a width of 12 inches (305 mm). Although the embodiment of the invention described here utilizes polyethylene, the method and apparatus of the current invention also can be used with other thermoplastic films.

The storage means 11 for the film is an unwind roll and the film is unwound by surface tensioning with an unwind tension of approximately 0.1 to 0.7 pounds (0.44–3.1 N) of tension over the full film width.

Figure 4:
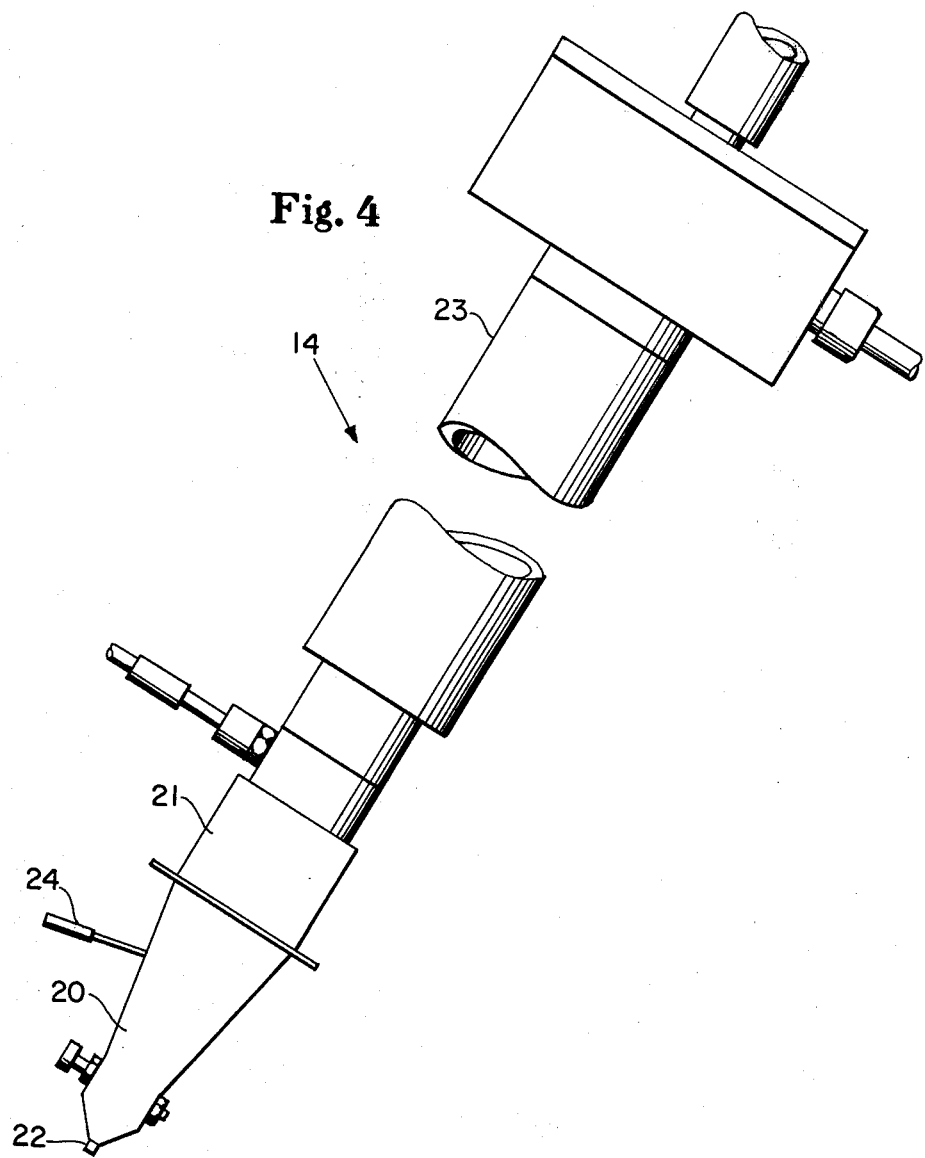
FIG. 4 shows a side elevational view of the heater means used in the current invention.

Heating means 14 comprises air heating nozzles. The nozzle comprises a lower plenum 20 and an upper plenum 21 (see FIG. 4) fabricated from thin stainless steel sheet metal. The lower plenum 20 is tapered and forms a slot 22 having a width of approximately 0.1 inches (2.5 mm) and a length of 12 inches (305 mm). The heating means 14 is mounted such that the width dimension of this slot 22 preferably overlies the entire width of the film 10. Upper plenum 21 has openings for electric heaters 23 which heat air to be blown through the slot 22. The electric heaters have a rating of 6 kilowatts at 240 volts to heat air to a maximum of 1200° F. (650° C.). The air heaters are manufactured by GTE Sylvania Emmissive Products, Exeter, N.H. Air temperature is controlled through thermocouples 24 in lower plenum 20 and voltage control loops (not shown) to the air heaters 23. The heaters discharge about 115 SCFH of air per lineal inch of slot length (1.28 standard $m^3$ per hour per lineal cm of slot length) at a temperature typically controlled at 360° F. (182° C.). Slot 22 of the nozzle is positioned approximately 0.5 inches to 1 inch (13–25 mm) above the thermoplastic film as seen in FIG. 1.

After being heated, the film is placed in intimate contact with the embossing surface 16 of embossing roll 13. Embossing roll 13 rotates in a clockwise direction about rotatable axle 25 pulling film 10 with it. Embossing roll 13 is powered by conventional means not shown.

Figure 2:
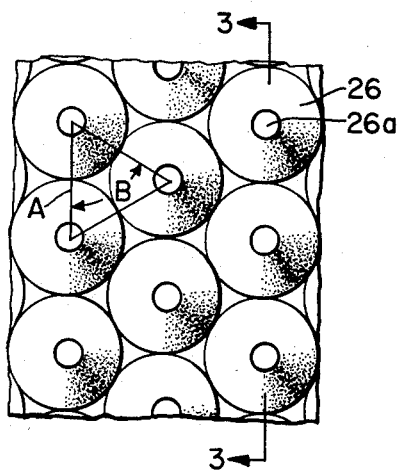
FIG. 2 shows an enlarged elevational view of the male embossing pattern on the embossing roll.
Figure 3:
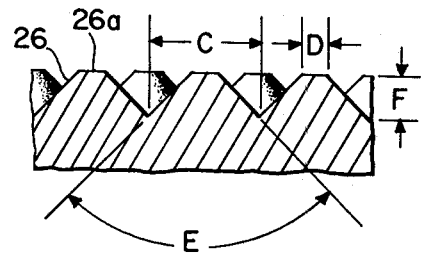
FIG. 3 shows a side elevational view of the male embossing pattern taken along line 3—3 of FIG. 2.

Embossing surface 16 is a male patterned embossing surface having a plurality of embossing knobs comprising closely packed truncated cones 26. As seen in FIG. 2, cones 26 are in close packed array with the center of rotation of each truncated cone forming an equilateral triangle with the other centers of rotation of the close packed cones having a dimension A equal to 0.040 inches (1.02 mm) and an angle B between sides equal to 60°. FIG. 3 shows a cross-sectional view of the embossing surface 16 through section line 3—3 in FIG. 2. As seen in FIG. 3, truncated cones 26 have a base diameter C equal to 0.040 inches (1.02 mm) and a top diameter D equal to 0.010 inches (0.25 mm), an angle of incline of opposite sides of the cones E equal to 90° and each cone has a height from the base to the flat truncated surface F equal to 0.015 inches (0.38 mm). Embossing roll 13 has approximately 217,420 bosses on its embossing surface. The flat apices 26a of the truncated cones 26 form an outside peripheral circumferential surface in embossing roll 13 with an outside diameter of 8.030 (203.96 mm) inches and a roll diameter across the cone bases of 8.000 (203.20) inches. While the diameter shows truncated cones as the raised knobs in the embossing surface, one skilled in the art could also utilize other shapes for the raised embossing knobs.

Embossing roll 13 is a hollow steel cylinder having a hollow interior space 27 and water passages 28 through axle 25 for the passage of water through embossing roll 13 facilitating cooling the surface of the roll. The steel roll is made of No. 4142 steel hardened to Rockwell Scale C58. In a preferred embodiment, embossing roll 13 has an outside diameter of 8.030 inches (203.96 mm), and inside diameter of 5.12 inches (130 mm), a total roll width of 13.0 inches (330 mm) and an embossing surface 16 width of 12.0 inches (304 mm). A steel roll with an outer embossing surface of close packed cones can be purchased from Inta-Roto, Inc., Richmond, Va. The embossing surface having a series of close packed cones, must be shaped on its outer cylindrical surface to create an embossing pattern of truncated cones of the dimensions specified above.

Embossing roll 13 is driven through a chain transmission by a 0.5 horsepower (0.37 kw) variable speed DC motor. The surface speed of embossing roll 13 is 31 feet per minute (15.7 cm/sc). Pressure rolls 15 and 18, and perforating roll 17 are rotated through friction arising from contact with embossing roll 13. The embossing roll 13 may be sprayed with silicone oil prior to contact with the film to facilitate release of the film from the roll after perforation.

First pressure roll 15 is a silicone rubber coated steel cylinder rotating about axis 29 which is fitted in bearings 30. For clarity, only one side of the apparatus is shown and only one of a pair of mechanisms mounted on any roller is shown. Bearings 30 are slidably mounted in channels 31 and can be moved in channels 31 by pressure cylinders 32. Pressure cylinders 32 can be used to adjust the position of bearings 30 and thus adjust the pressure applied to the film 10 at the nip of pressure roll 15 and embossing roll 13. Pressure roll 15 is made of cold rolled steel and has an elastomeric coating 33 consisting of silicone rubber having a hardness of 50 Durometer on the A scale. First pressure roll 15 has a silicone rubber coat 33 with an outside diameter of 8.0 inches (203 mm) applied to a steel cylinder having an outside diameter of 7.5 inches (190 mm), and an inside diameter of 5.5 inches (140 mm) and a roll width of 15.00 inches (381 mm). Silicone rubber coat 33 has a width on the cylinder of 13 inches (330 mm).

The first pressure roll 15 functions to force heat softened film 10 against embossing surface 16 where it acquires an embossed shape matching embossing surface 16. Embossing surface 16 causes the film to have a series of bosses shaped as truncated cones across the entire width of the film to be used as an end product.

After the film is embossed onto the embossing surface of embossing roll 13 and has acquired the shape of the truncated cones 26 of embossing surface 16, the film is then contacted with the outer circumferential surface 17a of perforating roll 17 to perforate each boss on the film on the truncated surface 26a of each cone. The perforating roll 17 is a hollow steel roll ground to a smooth surface on the outside and inside. The roll is made from No. 4130 steel tubing hardened to a hardness of Rockwell Scale C-35. The perforating roll 17 has an outside diameter of 4.0 inches (102 mm), a wall thickness of 0.16 inches (4.06 mm) and the length of 10.00 inches (254 mm). The inside circumferential wall of the perforating roll 17 is blackened to allow for increased heat absorption.

Inside the perforating roll 17 extending throughout the length of the perforating roll 17 is a heater 34. Heater 34 is a quartz infrared lamp which heats the roll to a temperature of 300°–500° F. (149°–260° C.).

Perforating roll 16 freely rotates without an axle and is pressed against embossing roll 13 and held captive by two solid rolls 35 and 36. Roll 35 is mounted on axles 37, roll 36 is mounted on axles 38 and axles 37 and 38 are mounted on frames 39. Frames 39 are pivotally mounted to the main frame via pivot 40 so as to move about pivot 40 to apply pressure to the perforating roll 17. On the opposite end of frame 39 from pivot 40 are mounted two pressure cylinders 41 which are also mounted on the main frame. Pressure cylinders 41 are adjustable to vary the pressure which is exerted against perforating roll 17 by solid rollers 35 and 36 and thus vary the pressure exerted by perforating roll 17 against the film on embossing roll 13. Perforating roll 17 rotates freely and is not supported by an axle or similar apparatus. Perforating roll 17 is kept in lateral alignment with embossing roll 13 by two cam followers (not shown) which contact the axial edges of the rotating perforating roll 17.

The perforating roll is a resilient, flexible roll with a wall thickness calculated to provide deflection necessary to maintain full length contact with film 10 on the embossing surface 16 of embossing roll 13. The perforating roll must contact the embossing roll over its entire width in order to perforate the film over the entire width of interest. It has been found that when a load of 90 pounds per lineal inch 158 N per lineal cm) is applied to the perforating roll 17, through rolls 35 and 36 by cylinders 41, it will maintain contact with embossing roll 13 across the entire width of the embossing roll 13 and result in a total deflection of the perforating roll 17 of approximately 0.007 inches (0.18 mm).

Contact of the heated outer circumferential surface of the perforating roll 17 with the film embossed upon the truncated surfaces 26a of the truncated cones 26 on embossing surface 16 create holes or perforations in the film on the truncated surface 26a of the cones of the embossing surface at the area of the nip between the embossing roll 13 and perforating roll 17.

After the film has been perforated by perforating roll 17, the film maintains registration and contact with the male patterned embossing surface 16 of the embossing roll 13 as it rotates. The film is contacted by a second pressure roll 18. The second pressure roll 18 forces the film back over the truncated cones 26 of the embossing surface 16 to conform the film to the embossing surface 16 to ensure that any residual memory in the thermoplastic film has not caused the film to lose its embossed shape during perforation.

The second pressure roll 18 is a hollow aluminum roll having hubs 42 welded on the ends of the rolls and mounted on shaft 43. Roll 18 has a silicone rubber coating 44 around the outside circumferential surface of the roll 18. Shaft 43 is supported by bearings attached to pivoting members 45. Members 45 are pivotally mounted to the main frame via pivots 46 on one end of each member 45 and by pressure cylinders 47 attached to members 45 at pivots 48 on the other end. Cylinders 47 are attached to the main frame. Pressure cylinders 47 are adjustable to move pivoting member 45 and roll 18 against film 10 which is still in registration and contact with embossing surface 16 of embossing roll 13. By adjusting pressure cylinders 47, pressure roll 18 can be pressed against film 10 to cause the film to conform to the embossing surface 16 of embossing roll 13.

Second pressure roll 18 is made of aluminum alloy having a cylindrical silicone rubber coating 44 of a hardness of 50 Durometer on the A scale. The aluminum roll has an outside diameter of 4.5 inches (114 mm), an inside diameter of 3.5 inches (89 mm), the silicone rubber coat has an outside diameter of approximately 5 inches (127 mm) and the width of both the roll and its rubber coating is 10 inches (254 mm). During operations, pressure roll 18 contacts film 10 directly and is driven by friction of contact with film 10 on embossing roll 13.

After a second embossing of the film caused by pressure applied to film 10 by pressure roll 18, the film is wound off on embossing roll 13 and over idler roller 19 to a rewind stand in its embossed condition.

In the method of this invention, the film 10 is rolled from storage means 11 and passes under the slot 22 of heating means 14. Heating means contacts the thermoplastic film 10 with hot air to preheat the film between 200°–300° F. (93°–149° C.). Film 10 is then applied to the embossing surface 16 of embossing roll 13 through the application of pressure by pressure roll 15. Hydraulic cylinders 32 apply approximately 4600 pounds (20460 N) of force through pressure roll 15 to film 10 on embossing surface 16 of embossing roll 13. Contact length of the nip between the pressure roll 15 and embossing roll 13 is 13 inches (330 mm) and the resulting specific loading is 350 pounds per lineal inch (613 N per lineal cm).

The pressure from pressure roll 15 places the film in intimate contact with and conforms it to the raised knobs of the male patterned embossing surface 16 of embossing roll 13. The circulating water in embossing roll 13 maintains the temperature at the outer circumferential surface of the embossed surface 16 between 100° and 175° F. (38°–79° C.). Where the film is in intimate contact with embossing surface 16, the film will stay at essentially the temperature of the outer embossing surface 16 substantially throughout the distance that it rotates in contact with the embossing surface 16.

The temperature of film 10 momentarily rises to a higher temperature during contact with the perforating roll 17. As the film is rotated near the perforating roll, it will be heated by radiant heat from perforating roller 17 and the temperature of the film will rise above the surface temperature of the embossing roll during exposure to infrared radiation from perforating roll 17.

After the film has been conformed to embossing surface 16 from the pressure applied by pressure roll 15, the film then rotates with embossing roll 13 through the nip of contact with perforating roll 17. Perforating roll 17 is heated by internal heater 34, which is a quartz lamp, which heats the contact surface of the perforating roll 17 to a temperature between 300°–500° F. (149°–260° C.) and preferably to a temperature of 475° F. (246° C.). Perforating roll 17 is pressed against film 10 on embossing roll 13 through the action of air cylinders 41 pivoting frame 17 and applying pressure to the perforating roll through rolls 35 and 36. Total force applied to press perforating roll 17 against embossing roll 13 is about 900 pounds (4000 N) and the contact length between the two rolls is 10 inches (254 mm), yielding a specific loading applied by the perforating roll of 90 pounds per lineal inch (158 N per lineal cm). Pressure exerted by the perforating roll on the film on embossing surface 16 extrudes the film material out of the contact area of the perforating roll 17 and the flat surfaces 26a of the truncated cones 26 on embossing surface 16. The material extruded from the hole area forms a grommet-like reinforcing rim around the perforation.

In area close to, but not in contact with the perforating roll, the film 10 is heated due to radiation from the surface of the perforating roll 17. Because some thermoplastic films have memory, the heat may cause the embossed material to begin to reform into a flat shape and lose its embossing. Because of this memory, it is advantageous to subject the film to a second pressurizing force which causes the film to reconform to the embossing surface 16.

After leaving the nip of the embossing roll 13 and the perforating roll 17, a film 10 rotates with the embossing roll to a nip with a second pressure roll 18 and embossing roll 13. At the nip between the second pressure roll 18 and embossing roll 13, pressure is exerted on roll 18 by pressure cylinders 47 and pivoting frame 45 to cause the film 10 to be embossed into intimate contact with the male patterned embossing surface 16. Silicone rubber surface 44 of pressure roll 18 forces the film to reacquire the shape of the truncated cones 26 on embossing surface 16. Pressure cylinders 47 exert a total force of around 3200 pounds (14230 N) on pressure roll 18 over the contact length between roll 13 and pressure roll 18 of about 10 inches (254 mm). This results in a specific loading applied by the second pressure roller 18 to film 10 of approximately 320 pounds per lineal inch (560 N per lineal cm). The second embossing step causes film 10 to conform to the embossing surface 16 of embossing roll 13 and retake the form of truncated cones 26.

After leaving the nip of second pressure roll 18 and embossing roll 13, film 10 passes over idler roller 19 and is wound into a roll on the rewind stand (not shown). Once leaving the surface of embossing roll 13, the film returns to ambient temperature.

The resulting product from this method is a film embossed with a closely packed array of truncated cones wherein the tip of each truncated cones is perforated. The resulting product has cones having a pitch of approximately 0.040 inches (1.02 mm); the included angle of the sides of each cone is approximately 90°; each cone having a perforation in its apex with a diameter of approximately 0.010 to 0.012 inches (0.25-0.30 mm); the aperture in each cone being slightly eliptical; and the resulting truncated cones on the embossed film having a cone height slightly less than cone 26 on the embossing surface 16 of embossing roll 13. As can be seen by one skilled in the art, the geometry of the bosses in the embossed film can be varied by varying the geometry on perforating surface 16 of embossing roll 13.

The embossed and perforated film resulting from the application of the above disclosed method results in thermoplastic film having a plurality of tapered bosses having perforations in the tips of each boss. The film can be used in combination with absorbent means to create an absorbent device wherein the film is located adjacent to the absorbent means with the tapered perforated bosses facing into the absorbent means. The bosses present a structure having decreasing cross section to liquid which transports the liquid into the absorbent means, through the perforations, by capillary action. The shape of the pore prevents movement of liquid through the perforated bosses from the absorbent means to outside the thermoplastic film. The perforated bosses freely allow the passage of vapor thoughout the perforated film.

EXAMPLE

A perforated, embossed film is made by the method of this invention on apparatus similar to that disclosed in FIG. 1. VisQueen polyethylene film, 12 inches (305 mm) wide and 0.001 inches (0.025 mm) thick, is unwound from unwind roll 11 over an idler roll 12 and onto an embossing roll 13. The embossing roll will pull the film from the unwind roll at a film tension of approximately 0.4 pounds (1.78 N) over the full film width. The film is heated by heating means 14, air heaters, which are located approximately 0.7 inches (17.8 mm) above the film to heat the film by directing a jet of hot air against the film in a direction approximately perpendicular to the film direction. The air heaters direct 115 SCFH per inch width of film (1.28 meter$^3$ hour/lineal cm of slot length at a nozzle temperature of 359° F. (182° C.). The thermoplastic film is pulled through the apparatus by the rotation of the embossing roll 13 which has a surface speed of 31 feet per minute (15.75 centimeter per second). The embossing surface 16 of the embossing roll is heated by contact with the perforating roll 17 and the warm film and has a surface temperature in the center of 130° F. (54.4° C.).

The film is embossed over the male patterned embossing surface 16 of embossing roll 13 through the pressure applied to the film by first pressure roll 15. Pressure is applied by cylinder 32 to the first pressure roll 15 to yield a specific loading on the first pressure roll 15 of 352 pounds per lineal inch (616 N/cm) to force the film over the embossing surface 16. The central portion of the first pressure roll is heated to 144° F. (62.2° C.) by residual heat on the embossing roll as a result from contact with a perforating roll and as a result of contact with heated air being emitted by heating means 14 which is located adjacent the pressure roll.

As the film rotates around embossing surface 16 of the embossing roll 13, it is perforated by contact with perforating roll 17. The temperature of the outer circumferential surface of the perforating roll is 476° F. (247° C.) which, on contacting the film overlaid on the embossing surface, melts the film and extrudes it from the surface to perforate the film. The perforating roll is sprayed with small amounts of silicone oil to prevent the thermoplastic film from sticking to the surface of the perforating roll. Pressure cylinder 41 exerts pressure on frame 39 through the solid rolls 35 and 36 to apply pressure to the perforating roll 17 yielding a specific loading of the perforating roll against the film overlaid on the embossing roll of 91.3 pounds per lineal inch (160 N/cm).

The polyethylene film rotates around with and in intimate contact with male patterned embossing surface 16 on embossing roll 13 where it is embossed for a second time as a result of pressure applied by a second pressure roll 18 to conform the film to the male patterned embossing surface 16. Pressure cylinder 47 exerts pressure on the second embossing roll through members 45 to yield a specific loading on the second pressure roll 18 of 326 pounds per lineal inch (570 N/cm). The second embossing steps conforms the film to the surface of the male patterned embossing surface to yield an embossed and perforated film.

Figure 5:
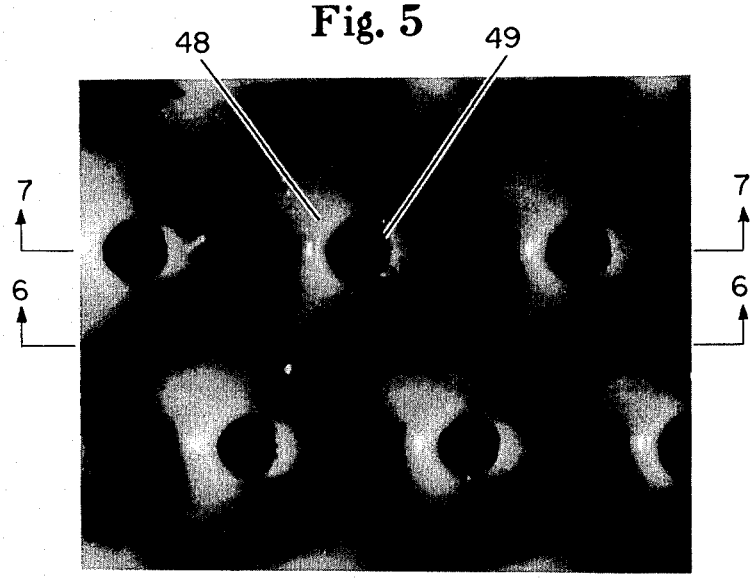
FIG. 5 is a photograph of a plan view of the product of the invention magnified 36 times.
Figure 6:
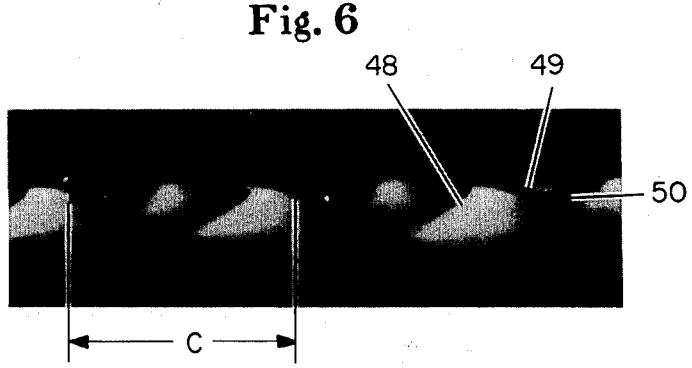
FIG. 6 is a cross-sectional view taken through section lines 6—6 in FIG. 5.
Figure 7:
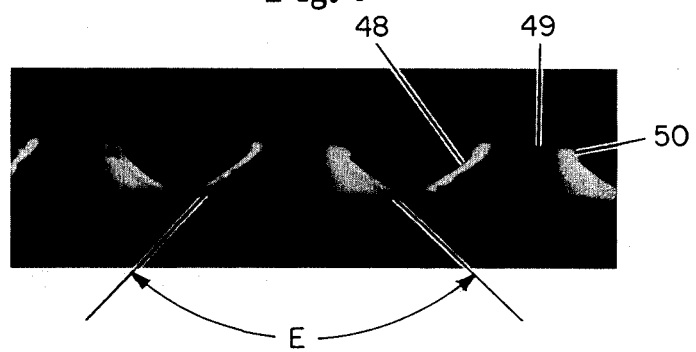
FIG. 7 is a cross-sectional view taken through section lines 7—7 in FIG. 6.

The final resulting product of a film resulting from the application of this method through the use of the above disclosed apparatus yields an embossed and perforated film as seen in FIGS. 5-7, consisting of a close packed triangular array of truncated cones 48 with perforated truncated top surfaces 49. The triangular array of close packed cones have a base diameter C equal to 0.04 inches (1.02 mm) having an included top angle E of 90° and having perforation on the apex of each cone which is slightly eliptical, with a major axis of approximately 0.012 inches (0.305 mm) in the direction of web movement and a minor axis of approximately 0.011 inches (0.279 mm) in a perpendicular direction. The cone height is slightly less than the cone height of the embossing surface 16 [0.015 inches (0.038 mm)]. The melting and extruding of thermoplastic film at the top of 26a of each truncated cone yields a grommet-like structure 50 around each perforation.

The method and apparatus described above as can be seen by one skilled in the art, are merely exemplary and may be varied within the scope of the invention.

What is claimed is:

1. A method to produce an embossed thermoplastic film and to perforate the tips of the bosses thereof, comprising the following steps:
   (a) supplying a heated, deformable thermoplastic film to a male patterned embossing surface having a multiplicity of raised knobs with apices which define a raised surface;
   (b) conforming the thermoplastic film into intimate contact with the raised knobs of the male patterned embossing surface to produce an embossed film having a multiplicity of raised bosses;

(c) perforating the bosses of the film by pressing the tips of said raised bosses between said apices of said knobs and a heated perforating surface to form apertures in the apices of said raised bosses, while maintaining registration and contact between said film and said raised knobs;

(d) cooling said embossed film to a less deformable state while maintaining registration and contact between said embossed film and said raised knobs; and (e) removing said embossed film from said male patterned embossing surface.

2. The method as claimed in claim 1 wherein the film supplied is polyethylene.

3. The method as claimed in claim 1 wherein there is the added step of cooling the embossing surface by a cooling means to a surface temperature between 100°–175° F. (38°–79° C.).

4. The method as claimed in claim 1 wherein the step of perforating the film is performed by applying a heated perforating surface to a thermoplastic film overlaid on a male patterned embossing surface at a pressure of 90 pounds per lineal inch.

5. The method as claimed in claim 1 wherein the heated perforating surface is a resilient hollow metal roll.

6. The method as claimed in claim 5 wherein there is the step of heating the resilient, hollow metal roll through radiant heat provided by radiant heat means inside the hollow resilient metal roll.

7. The method as claimed in claim 5 wherein there is the step of rotating the perforating roll freely against the male patterned embossing surface.

8. The method as claimed in claim 6 wherein the resilient, hollow metal roll is heated by radiant heat means inside the hollow resilient metal roll to a temperature of between 300°–500° F. (194°–160° C.) and preferably to 475° F. (246° C.).

9. The method as claimed in claim 1 wherein there is the step of heating the thermoplastic film before supplying the film to the embossing surface.

10. The method as claimed in claim 9 wherein the thermoplastic film is initially heated to a temperature of between 200°–300° F. (93°–149° C.).

11. The method as claimed in claim 1 wherein said conforming comprises applying a first pressure to said film through a first pressure roll by interposing the film between the surface of a first pressure roll and the embossing roll causing it to conform to male patterned embossing surface.

12. The method as claimed in claim 11 wherein said step of applying a first pressure to said film applies a pressure of 350 pounds per lineal inch to the thermoplastic film overlaid on male patterned embossing surface.

13. The method as claimed in claim 1 or 11 wherein after the step of perforating the film there is the step of a second conforming of the raised bosses in the film to the raised knobs of the male patterned embossing surfaces.

14. The method as claimed in claim 13 wherein the step of a second conforming of the film comprises applying pressure to the film on the embossing surface by applying pressure to a second pressure roll and interposing the film between the second pressure roll and the embossing roll.

15. The method as claimed in claim 14 wherein there is the step of maintaining the thermoplastic film in at least registration and contact with the peripheral surface of the embossing surface during the period from the first conforming of the film into bosses in intimate contact with the raised knobs of the male patterned embossing surface, through perforating the boss and the second conforming of the film into intimate contact with the raised knobs of the male patterned embossing surface.

16. The method as claimed in claim 14 wherein the step of a second conforming of the film comprises applying 320 pounds per lineal inch of pressure by the second pressure roll against the embossed thermoplastic film on the male patterned embossing surface.

* * * * *